United States Patent [19]

Kulig

[11] Patent Number: 4,580,045

[45] Date of Patent: Apr. 1, 1986

[54] APPARATUS FOR THE INSPECTION OF GLASSWARE FOR LEANERS AND CHOKES

[75] Inventor: Constantine W. Kulig, Windsor, Conn.

[73] Assignee: Emhart Industries, Inc., Farmington, Conn.

[21] Appl. No.: 725,509

[22] Filed: Apr. 22, 1985

Related U.S. Application Data

[63] Continuation of Ser. No. 405,673, Aug. 6, 1982.

[51] Int. Cl.[4] .......................................... G01N 21/00
[52] U.S. Cl. ............................. 250/223 B; 356/240
[58] Field of Search ................... 250/223 B; 356/240; 209/524–526, 529; 358/106

[56] References Cited

U.S. PATENT DOCUMENTS

| | | | |
|---|---|---|---|
| 4,256,957 | 3/1981 | Ford et al. | 250/223 B |
| 4,284,353 | 8/1981 | Yoshida et al. | 250/223 B X |
| 4,335,960 | 6/1982 | Ashcroft et al. | 356/240 |
| 4,424,441 | 1/1984 | Bieringer et al. | 250/223 B |
| 4,435,641 | 3/1984 | Hajime | 250/223 B |

Primary Examiner—Edward P. Westin
Attorney, Agent, or Firm—Arthur B. Moore

[57] ABSTRACT

An inspection device is disclosed for inspecting glass containers for leaners and chokes as they are moved continuously past a single work station. The invention utilizes a video camera and processing circuits for determining the size of the opening of the finish of each container as well as the extent of its lean relative to predetermined acceptable limits. Containers having excessive lean or choke are rejected.

2 Claims, 5 Drawing Figures

4,580,045

APPARATUS FOR THE INSPECTION OF GLASSWARE FOR LEANERS AND CHOKES

This is a continuation of co-pending application Ser. No. 405,673, filed on Aug. 6, 1982.

BACKGROUND OF THE INVENTION

1. Field of the Invention

The invention relates generally to inspection devices for the inspection of glass containers. More particularly, the invention relates to apparatus for inspecting glass containers for leaners and chokes.

2. Description of the Prior Art

Devices or gauges exist in the prior art for the inspection of glass containers, generally bottles, for conditions or parameters known as lean and choke. The term "lean" refers to the extent to which the top of the bottle deviates in alignment from its base. The term "choke" refers to the opening in the top portion, or finish, of the bottle. A bottle with either an excessive lean or a restricted opening is defective and must be rejected.

All known prior art choke gauges and most leaner gauges require contact with the bottle being inspected, some such devices also require stopping the bottle. Consequently such devices make the inspection process relatively slow, complex and not ideally suitable for today's high speed glass container production equipment.

Also, leaner gauges are often separate devices from choke gauges therefore requiring the use of two inspection stations to perform these functions. Most prior art inspection for leaners and chokes has therefore been relatively inefficient, costly and slow.

Furthermore, prior art leaner and choke gauges are often of the mechanical type. The former use a fixed ring gauge to check each bottle for excessive lean while the latter use a fixed plug gauge to check for restricted openings. Such devices are not capable of being easily adjusted to alter the amount of allowable lean or choke. Accordingly, there is a need for a single non-contact leaner and choke gauge capable of rapid adjustment of allowable parameters.

A prior art non-contact leaner gauge, disclosed in U.S. Pat. No. 4,107,523, is an apparatus that detects leaners by illuminating the rim of the finish of the bottle and detecting the reflected light. This device is rather complex, requires careful alignment for proper operation, does not provide any information about the amount of the lean and is not capable of being easily adjusted. An adjustable, non-contact leaner gauge has been disclosed in U.S. Pat. No. 3,549,890. However, this device is also complex, costly and incapable of inspecting for chokes. No prior art choke gauge is known capable of easy adjustment of the extent of choke.

In view of the above it is an object of the present invention to provide an apparatus for detecting leaners and chokes at a single inspection station, without contact with the bottle and without stopping any bottle. It is a further object to provide an apparatus wherein the parameters representative of the lean and choke of defective bottles may be easily adjusted.

SUMMARY OF THE INVENTION

These and other objects are achieved by the preferred embodiment of the invention disclosed herein which is an apparatus for inspecting a bottle moving continuously on a conveyor past a work station and comprising:

light source means for illuminating the interior of said bottle at said work station;

trigger means for detecting the position of said bottle at a predetermined point relative to said work station;

a video camera responsive to said trigger means for viewing the opening of said bottle, said video camera aligned substantially along the vertical centerline of said bottle when said bottle is at said predetermined point;

processing means responsive to said camera and said trigger means for determining at least one predetermined parameter of said opening;

means for comparing said parameter to a predetermined standard;

means responsive to said comparator means for rejecting said bottle in the event said parameter bears a predetermined relationship to said standard.

DESCRIPTION OF THE PREFERRED EMBODIMENT

Figure 1:
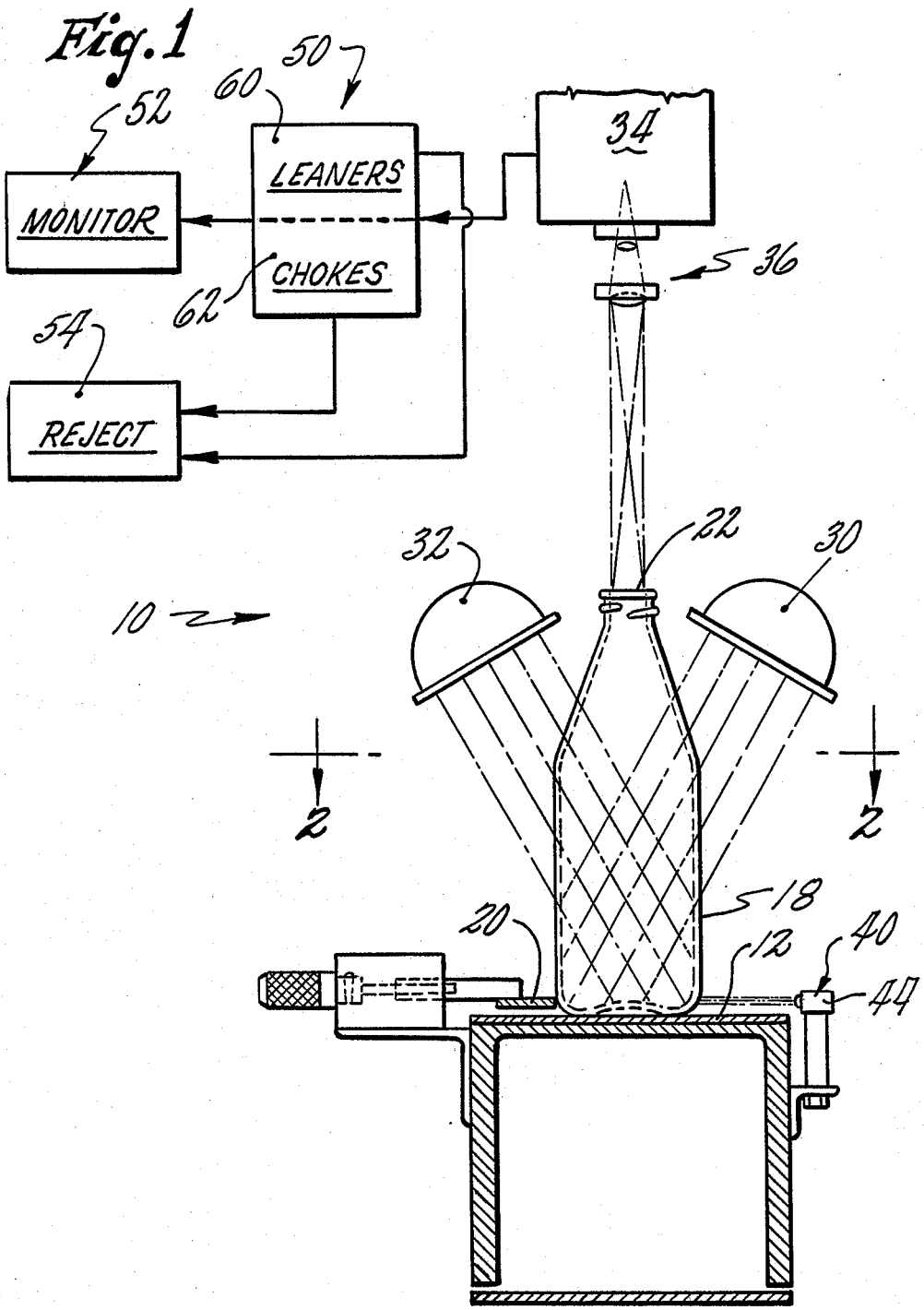
FIG. 1 is a diagrammatic elevational view of the invention situated adjacent a conveyor for carrying glass containers to be inspected.
Figure 2:
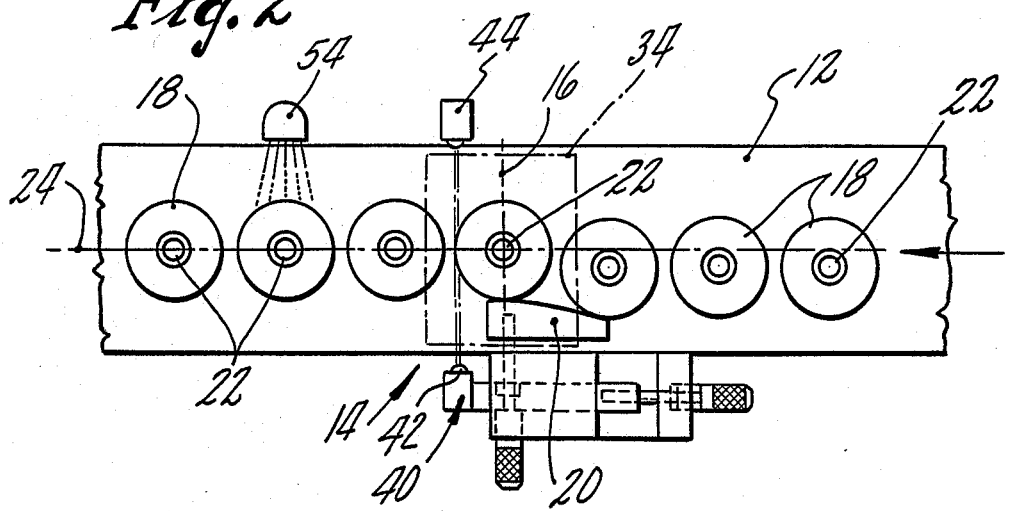
FIG. 2 is a plan view of FIG. 1 taken along the lines 2—2.

Referring now to FIGS. 1 and 2 there is shown a leaner and choke gauge 10 constructed according to the principles of the present invention. Gauge 10 is situated adjacent conveyor 12 at work station 14 which is aligned along transverse centerline 16 for the inspection of bottles 18 as they are moved continuously past work station 14. Guide means 20 is utilized to laterally position the bottles so that the opening 22 of each bottle passes the intersection of transverse centerline 16 with the axis 24 of conveyor 12.

A pair of light sources 30 and 32 (best seen in FIG. 1) are arranged to illuminate the interior of each bottle as it passes work station 14. The light intensity required is obviously a function of the degree of translucence of the bottle. Video camera 34 is focused through a lens system 36 to view the opening 22 of each bottle as it passes transverse centerline 16. A trigger mechanism 40 comprising light emitter 42 and detector 44 is aligned parallel to transverse centerline 16 at a predetermined distance therefrom and senses the passage of the leading edge of each container 18 (near its base) through a work station 14. In operation, trigger mechanism 40 produces a triggering signal at a time when the opening 22 of bottle 18 should be centered about the intersection of lines 16 and 24.

Figure 3:
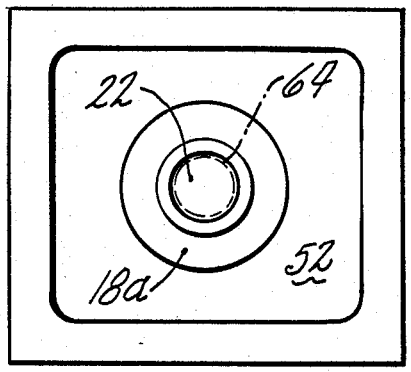
FIGS. 3, 4 and 5 are diagrammatic views of a monitor screen showing a plan view of a representative ideal bottle, leaner and choke, respectively.

Video camera 34 is aligned substantially along the vertical centerline of the bottle located at the work station and produces an instantaneous image of opening 22 in response to the triggering signal produced by trigger mechanism 40. The video image may be continuously produced by camera 34 as the bottle is moving provided the image is "frozen" in response to the triggering signal. The video signal produced by camera 34 passes through processing circuit 50 to monitor 52. FIG. 3 represents a diagrammatic view of the monitor screen representing the camera's view of a representative "ideal" bottle 18a, i.e. a bottle having its vertical axis concentric with its base and opening and having a predetermined size opening. As will be explained below, processing circuit 50 processes the instantaneous video signal to determine which bottles are unacceptable due to excessive lean or choke. The circuits would then provide an appropriate signal to reject mechanism 54 situated downstream from work station 14 to reject defective bottles.

Circuit 50 processes the video signal in two subcircuits 60 and 62 for calculating various parameters to determine which bottles are leaners and chokes, respectively. Subcircuit 60 computes the area subtended by opening 22 (as monitored on monitor 52, best seen in FIG. 3) and compares it to a standard area represented by circle 64 on the monitor screen. The standard area may be preset into subcircuit 60 or may be adjustable by an operator by means not shown. If the computed area for a bottle is found to be smaller than the standard by a predetermined adjustable amount, subcircuit 60 provides a signal to reject mechanism 54 to later reject that bottle for excessive lean. Similar results could be obtained by calculating the center of opening 22 and comparing it to a standard center. All bottles deviating by an excessive amount would be rejected.

Subcircuit 62 similarly determines whether a particular bottle has an excessive choke by computing the area subtended by opening 22 as well as computing the smallest diameter thereof. Both the computed area and smallest diameter are compared to predetermined adjustable standards and a bottle is rejected if it has computed parameters outside predetermined adjustable limits.

Subcircuits 60 and 62 are constructed of conventional components and are not shown or described in detail herein since the operations described with respect to each are deemed to be within the scope of those skilled in the art.

Figure 4:
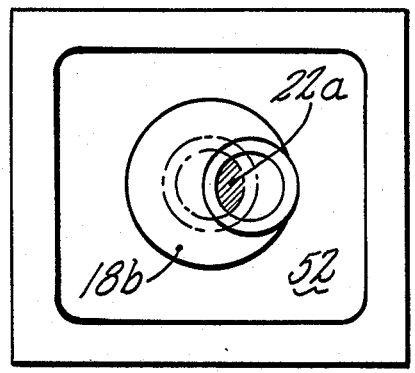
Figure 5:
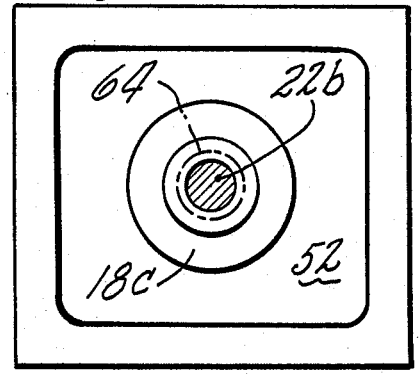

As shown in FIGS. 4 and 5, bottles 18*b* and 18*c* having excessive lean and choke respectively may result in identical area calculations 22*a* and 22*b*. (Note that the drawings do not necessarily show this condition.) Thus, calculation of areas 22*a* and 22*b* of opening 22 could be accomplished by one subcircuit 60 or 62 without any calculation of the smallest diameter of the opening. This would permit detection of leaners and chokes with simplified circuitry although it would not provide an indication of why a bottle was being rejected. If one desires to determine whether a bottle was rejected for lean or choke then some other parameter besides just area must be calculated.

It will further be understood by those skilled in the art that numerous modifications and improvements may be made to the preferred embodiment of the invention disclosed herein without departing from the spirit and scope thereof.

What is claimed is:

1. Apparatus for inspecting a bottle moving continuously on a conveyor past a work station, comprising:
    a light source for illuminating the interior of said bottle at said work station;
    trigger means for detecting the position of said bottle at a predetermined point relative to said work station;
    a video camera for viewing light from said light source at the opening of said bottle and for producing video signals representing an instantaneous image of said opening when said bottle is at the predetermined point, at which point said video camera is aligned substantially along a vertical center line of said bottle;
    processing means responsive to said video signal and said trigger means for determining the area of the opening of said bottle; and
    means for comparing said area with a predetermined minimum acceptable area of the bottle opening, and for causing rejection of the bottle if the area of said opening is less than said minimum acceptable area.

2. Apparatus for inspecting a bottle moving continuously on a conveyor past a work station, comprising:
    a light source for illuminating the interior of said bottle at said work station;
    trigger means for detecting the position of said bottle at a predetermined point relative to said work station;
    a video camera for viewing light from said light source at the opening of said bottle and for producing video signals representing an instantaneous image of said opening when said bottle is at the predetermined point, at which point said video camera is aligned substantially along a vertical center line of said bottle;
    processing means responsive to said video signal and said trigger means for determining the area of the opening of said bottle subtended by a standard center region; and
    means for comparing said subtended area with a predetermined minimum acceptable area and for causing rejection of said bottle if the subtended area is less than said minimum acceptable area.

* * * * *